US006355015B1

(12) United States Patent
Eek et al.

(10) Patent No.: US 6,355,015 B1
(45) Date of Patent: Mar. 12, 2002

(54) MEDICAL DEVICE FOR INTERNAL HEAT TREATMENT AND DRUG DELIVERY

(75) Inventors: Arne Eek, Trosa; Magnus Bolmsjö, Lund, both of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/308,584

(22) PCT Filed: Dec. 16, 1998

(86) PCT No.: PCT/SE98/02346

§ 371 Date: May 21, 1999

§ 102(e) Date: May 21, 1999

(87) PCT Pub. No.: WO99/30654

PCT Pub. Date: Jun. 24, 1999

(30) Foreign Application Priority Data

Dec. 17, 1997 (SE) .............................. 9704710
Dec. 17, 1997 (SE) .............................. 9704713

(51) Int. Cl.[7] .............................................. A61H 29/00
(52) U.S. Cl. ............................ 604/103.01; 604/101.05
(58) Field of Search ......................... 604/96.01, 99.01, 604/99.02, 99.03, 99.04, 101.01, 101.04, 101.05, 103.01, 21, 113, 114

(56) References Cited

U.S. PATENT DOCUMENTS

| | | | |
|---|---|---|---|
| 3,875,939 A | | 4/1975 | Bolduc et al. ............... 128/235 |
| 3,972,331 A | | 8/1976 | Bolduc et al. ............... 128/232 |
| 4,994,033 A | | 2/1991 | Shockey et al. ............ 604/101 |
| 5,336,178 A | | 8/1994 | Kaplan et al. ................ 604/53 |
| 5,380,319 A | | 1/1995 | Saito et al. ................... 606/28 |
| 5,505,730 A | * | 4/1996 | Edwards ....................... 606/41 |
| 5,531,707 A | | 7/1996 | Kers et al. .................. 604/200 |
| 5,569,198 A | * | 10/1996 | Racchini ...................... 604/96 |
| 5,578,008 A | * | 11/1996 | Hara ............................ 604/96 |
| 5,843,033 A | * | 12/1998 | Ropiak ........................ 604/96 |

FOREIGN PATENT DOCUMENTS

| | | | |
|---|---|---|---|
| HU | 180047 | 5/1982 | .......... A61M/31/00 |
| HU | 213 805 | 12/1993 | .......... A61M/31/00 |
| WO | WO 91/18640 | 12/1991 | .......... A61M/31/00 |
| WO | WO 97/42998 | 11/1997 | .......... A61M/31/00 |

OTHER PUBLICATIONS

Abstract for AI 1 above.
Abstract for AJ 1 above.

* cited by examiner

*Primary Examiner*—Sharon Kennedy
(74) *Attorney, Agent, or Firm*—Michael A. Sanzo; Pillsbury Winthrop LLP

(57) ABSTRACT

Medical device (1) for effecting heat treatment and local delivery of a fluid medicament on body tissue presenting a predetermined section of a boundary wall of a passageway in a human or animal body comprising a catheter-like member (12) for insertion into the passageway to a predetermined insertion position, the catheter-like member being provided with an inflatable balloon structure (11) having a boundary wall which is inflatable against the body tissue when the catheter-like member (12) is in the predetermined insertion position and delivery means (2,11,25) for local delivery of the fluid medicament on the body tissue when the catheter-like member (12) is in the predetermined insertion position, and a heating arrangement (10,15) which is adapted to heat the body tissue when the catheter-like member (12) is in the predetermined insertion position. The delivery means (2,11,25) comprises a supply channel (25) for supply of the fluid medicament to the balloon structure (11) and a construction for the boundary wall (2) of the balloon structure (11) which is permeable to the fluid medicament. Supply of the fluid medicament to the balloon structure along the supply channel (25) when the catheter-like member (12) is in the predetermined insertion position thereby causes the balloon structure (11) to inflate and fluid medicament to be delivered locally on the body tissue through the boundary wall (2) of the balloon structure (11).

7 Claims, 1 Drawing Sheet

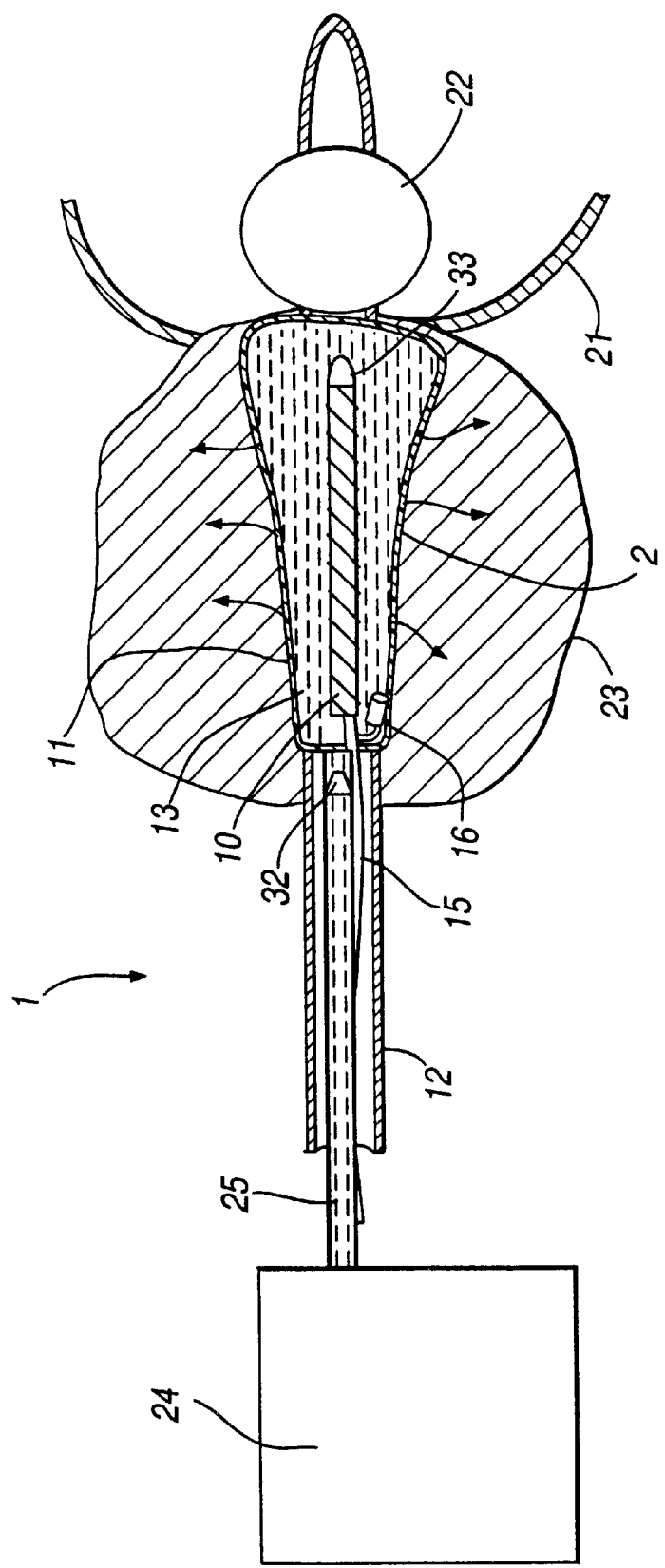

MEDICAL DEVICE FOR INTERNAL HEAT TREATMENT AND DRUG DELIVERY

CROSS REFERENCE TO RELATED APPLICATIONS

The present application represents U.S. national stage of international application PCT/SE98/023246 with an international filing date of Dec. 16, 1998. The international application claims priority to Swedish applications 9704710-4 and 9704713-8. Both of the Swedish applications were filed on Dec. 17, 1997.

FIELD OF THE INVENTION

The present invention relates to a medical device for effecting heat treatment and local delivery of a fluid medicament on body tissue presenting a predetermined section of a boundary wall of a passageway in a human or animal body comprising a catheter-like member for insertion into the passageway to a predetermined insertion position, the catheter-like member being provided with an inflatable balloon structure having a boundary wall which is inflatable against the body tissue when the catheter-like member is in the predetermined insertion position and delivery means for local delivery of the fluid medicament on the body tissue when the catheter-like member is in the predetermined insertion position, and a heating arrangement which is adapted to heat the body tissue when the catheter-like member is in the predetermined insertion position (hereinafter in part referred to as a "medical device of the type defined").

BACKGROUND OF THE INVENTION

U.S. Pat. No. 5,380,319 [Olympus Optical Co., Ltd.] makes known a medical device of the type defined which is adapted for treatment of cancerous tissues in a body passageway (hereinafter "the Olympus device"). The balloon structure of the Olympus device is inflated by supplying a liquid thereto and the heating arrangement comprises a heating element in the balloon structure. With regard to the delivery means, this comprises a supply path for the medicament which terminates at one or more discharge arrangements mounted on the outer surface of the boundary wall of the balloon structure. When the catheter-like member of the Olympus device is in the predetermined insertion position, the balloon structure is inflated by the supply of liquid thereto and the medicament delivered on the cancerous tissue from the one or more discharge arrangements. The heat treatment of the cancerous tissue is then effected by activating the heating element so that the liquid in the balloon structure is heated and acts as a medium for heat transfer to the body tissue through the boundary wall of the balloon structure.

The present invention proposes to provide a medical device of the type defined with means for combining the delivery of the medicament with inflation of the balloon structure.

SUMMARY OF THE INVENTION

According to the present invention there is provided a medical device of the type defined in which the delivery means comprises a supply channel for supply of the fluid medicament to the balloon structure and a construction for the boundary wall of the balloon structure which is permeable to the fluid medicament whereby supply of the fluid medicament to the balloon structure along the supply channel when the catheter-like member is in the predetermined insertion position causes the balloon structure to inflate and fluid medicament to be delivered locally on the body tissue through the boundary wall of the balloon structure. The boundary wall of the balloon structure may be constructed so as to be fluid permeable by being porous permeable or perforate. Ordinarily, the medicament would be in liquid form in which case the boundary wall of the balloon structure would be constructed so as to be liquid permeable.

In an embodiment of the invention such as the one hereinafter to be described the heating arrangement comprises a heating element which is adapted to heat the fluid medicament prior to its discharge from the catheter-like member whereby the body tissue is able to be heated by fluid medicament delivered locally thereon through the boundary wall of the balloon structure when the catheter-like member is in the predetermined insertion position. This could be achieved by placing the heating element in the balloon structure. Alternately, the heating element may be placed in the supply channel of the catheter-like member or in a source of the medicament for connection to the supply path of the catheter-like member. A greater heating efficiency of the body tissue would result from the direct delivery of heated medicament thereon as compared to the indirect heating of the body tissue achieved by the Olympus device. Moreover, heating of the medicament may improve its efficacy.

In an embodiment of the invention such as the one hereinafter to be described the device further comprises a source of a fluid anaesthetic for supply to the supply channel for local delivery on the body tissue through the boundary wall of the balloon structure when the catheter-like member is in the predetermined insertion position. Other types of medicament could, of course, be administered by the medical device of the invention, further non-limiting examples being antibiotics, anti-cancer agents and anti-inflammatory agents.

In an embodiment of the invention such as the one hereinafter to be described the medical device is for effecting heat treatment and local delivery of the fluid medicament on the prostate gland of a human male body with the catheter-like member being adapted for insertion into the urethra of the human male body to the predetermined insertion position in which the boundary wall of the balloon structure is inflatable against the prostate gland.

BRIEF DESCRIPTION OF THE DRAWING

The drawing is a partially sectional view of a device which includes the essential features of the invention.

DESCRIPTION OF EXEMPLARY EMBODIMENT OF THE INVENTION

By way of example, there will now be described with reference to the accompanying drawing a medical device 1 in accordance with the invention for prostate gland cancer treatment in a human male patient.

The medical device 1 is shown in its operative state with a treatment catheter 12 inserted into the urethra of the patient to an operational position to effect a heat treatment of the tissue of the prostate gland 23 in the environment surrounding the urethra to cause the tissue to die in a defined partial volume of the prostate gland 23 from the neck of the urine bladder 21 down towards the apex.

The treatment catheter 12 is provided with a receptacle or balloon 11 near the distal end thereof having a flexible, expandable and permeable boundary wall 2 made of elastic silicone, latex or other material with corresponding elastic properties. The receptacle 11 is connected through a supply channel 25 to a supply container 24 disposed extracorporeally which contains a supply of heatable liquid anaesthetic whereby the receptacle 11 is able to be expanded radially outwardly to the expanded state shown in the drawing on anaesthetic 13 being supplied to the receptacle 11 through the supply channel 25 from the supply container 24. A valve 32 is located in the supply channel 25 near to the receptacle 11 to prevent the anaesthetic 13 flowing back from the receptacle 11 and maintaining the desired pressure in the receptacle 11.

A heating device 10 is contained in the receptacle 11 for heating the anaesthetic 13 supplied to the receptacle 11 from the supply container 24. The heating device 10 is in the form of a resistance wire heated through supply of energy thereto through a cable 15 which is in turn connected to an energy supply unit disposed extracorporeally (not shown). Other forms of heating device could of course be used, for instance a Peltier element. The heating device is supplemented with a light fitting 33 to facilitate localisation and placement of the treatment catheter 12.

Also disposed in the receptacle 11 is a temperature transducer 16 which is operatively connected to a control unit (not shown) disposed extracorporeally to provide measurements of the temperature in the receptacle 11. The temperature measurements provided by the transducer 16 are used to control the energy supply unit and concomitantly the heating action of the heating device 10. The transducer may be in the form of a thermistor, thermocouple or optical transmitter.

Adjacent the distal tip of the treatment catheter 12 there is provided a securement balloon 22 which can be expanded in a conventional manner through a channel (not shown) in the treatment catheter 12.

As shown in the drawing, insertion of the treatment catheter 12 to the operational position places the securement balloon 22 in the urine bladder 21 and the receptacle 11 adjacent the prostate gland 23. Once the treatment catheter 12 is in the operational position the securement balloon 22 is expanded to secure the catheter 12 in place. Anaesthetic 13 is then supplied to the receptacle 11 to cause the receptacle 11 to expand outwardly into contact with the adjacent tissue of the prostate gland 23. Moreover, anaesthetic 13 passes through the permeable boundary wall 2 of the receptacle 11 to anaesthetise the adjacent prostate gland tissue. The heating device 10 is then activated to cause the anaesthetic 13 in the receptacle 11 to be heated. Heat is thus conveyed to the adjacent prostate gland tissue through the boundary wall 2 of the receptacle 11 and further by heated anaesthetic permeating through the boundary wall 2.

Upon completion of the heat treatment the receptacle 11 is cooled to body temperature and the anaesthetic 13 contained in the receptacle 11 evacuated back to the supply container 24.

Several advantages are attendant by using an anaesthetic as the conducting medium for heat treating body tissue which presents a section of a body passageway. Firstly, heating of the tissue can take place by direct action of the preheated anaesthetic on the body tissue giving an improved heating efficiency of the body tissue. Secondly, heating can be carried out at a higher temperature (90° C. plus) without undue pain being experienced by the patient which in the specific case of heat treatment of the prostate gland enables the prostate gland tissue to vascularise and become self-supporting thereby removing the need for a stent or other form of scaffold as is the case where the medical device made known in International patent application publication No. WO97/02794 (Lund Instruments AB) is used. Thirdly and finally, heating of the anaesthetic is thought to improve the anaesthetising action of the anaesthetic.

It will be appreciated by those versed in the art that the invention is not restricted solely to application in the treatment of cancer of the prostate gland but is equally applicable for other treatments requiring the heating of body tissue in a body passageway until the tissue dies such as in the treatment of illnesses with which unnatural tissue growth is associated, examples being cancers of the esophagus, trachea, ureter and intestines and benign prostate hyperplasia (BPH).

What is claimed is:

1. A medical device for effecting heat treatment and local delivery of a fluid medicament on body tissue presenting a predetermined section of a boundary wall of a passageway in a human or animal body comprising:

a catheter for insertion into the passageway to a predetermined insertion position, the catheter being provided with an inflatable balloon structure having a boundary wall which is inflatable against the body tissue when the catheter is in the predetermined insertion position;

delivery means for local delivery of the fluid medicament on the body tissue when the catheter is in the predetermined insertion position; and a heating arrangement which is adapted to heat the body tissue when the catheter is in the predetermined insertion position;

wherein the delivery means comprises a supply channel for supply of the fluid medicament to the balloon structure and a construction for the boundary wall of the balloon structure which is permeable to the fluid medicament, whereby supply of the fluid medicament to the balloon structure along the supply channel when the catheter is in the predetermined insertion position causes the balloon structure to inflate and fluid medicament to be delivered locally on the body tissue through the boundary wall of the balloon structure, and wherein the heating arrangement comprises a heating element which is adapted to heat the fluid medicament prior to its discharge from the catheter whereby the body tissue is heated by fluid medicament delivered locally thereon through the boundary wall of the balloon structure when the catheter is in the predetermined insertion position.

2. A medical device according to claim 1, wherein said catheter of said medical device is adapted for insertion into the urethra of a human male to a predetermined insertion position in which the boundary wall of the balloon structure may be inflated against the prostate gland of said male.

3. A medical device according to claim 1, wherein the fluid medicament is a fluid anaesthetic.

4. A medical device according to claim 1, wherein the fluid anaesthetic is the fluid medicament.

5. A medical device for effecting heat treatment and local delivery of a fluid medicament on body tissue presenting a predetermined section of a boundary wall of a passageway in a human or animal body comprising;

a catheter for insertion into the passageway to a predetermined insertion position, the catheter being provided with an inflatable balloon structure having a boundary wall which is inflatable against the body tissue when the catheter is in the predetermined insertion position;

delivery means for local delivery of the fluid medicament on the body tissue when the catheter is in the predetermined insertion position; and a heating arrangement which is adapted to heat the body tissue when the catheter is in the predetermined insertion positions;

wherein the delivery means comprises a supply channel for supply of the fluid medicament to the balloon structure and a construction for the boundary wall of the balloon structure which is permeable to the fluid medicament, whereby supply of the fluid medicament to the balloon structure along the supply channel when the catheter is in the predetermined insertion position causes the balloon structure to inflate and fluid medicament to be delivered locally on the body tissue through the boundary wall of the balloon structure, the device further comprising a source of a fluid anaesthetic for supply to the supply channel for local delivery on the body tissue through the boundary wall of the balloon structure when the catheter is in the predetermined insertion position.

6. A medical device according to claim 5, wherein said catheter of said medical device is adapted for insertion into the urethra of a human male to a predetermined insertion position in which the boundary wall of the balloon structure may be inflated against the prostate gland of said male.

7. A medical device for effecting heat treatment and local delivery of a fluid medicament on body tissue presenting a predetermined section of a boundary wall of a passageway in a human or animal body comprising:

a catheter for insertion into the passageway to a predetermined insertion position, the catheter being provided with an inflatable balloon structure having a boundary wall which is inflatable against the body tissue when the catheter is in the predetermined insertion position;

delivery means for local delivery of the fluid medicament on the body tissue when the catheter is in the predetermined insertion position;

a heating arrangement which is adapted to heat the body tissue when the catheter is in the predetermined insertion position; and an inflatable securement balloon structure fixedly connected to and in fluid communication with a securement balloon inflation channel provided in the catheter, the inflatable securement balloon structure adapted to (1) inflate and secure the catheter in the predetermined insertion position and (2) deflate and permit the withdrawal of the catheter from the passageway.

* * * * *